United States Patent [19]

Saunders et al.

[11] 3,944,537

[45] Mar. 16, 1976

[54] PREPARATION OF ALPHA-AMYLASE INHIBITOR

[75] Inventors: Robert M. Saunders, Albany; George O. Kohler, El Cerrito, both of Calif.

[73] Assignee: The United States of America as represented by the Secretary of Agriculture, Washington, D.C.

[22] Filed: Nov. 26, 1974

[21] Appl. No.: 527,401

[52] U.S. Cl. ............. 260/112 G; 426/321; 426/331
[51] Int. Cl.² ...................... A23J 1/12; C07G 7/00
[58] Field of Search .................................. 260/112 G

[56] References Cited
UNITED STATES PATENTS

| | | | |
|---|---|---|---|
| 2,538,898 | 1/1951 | Cleland et al. | 260/112 G UX |
| 2,597,566 | 5/1952 | Chiego et al. | 426/364 |
| 2,961,353 | 11/1960 | Carlson et al. | 260/112 G UX |
| 3,185,574 | 5/1965 | Gabby et al. | 426/152 |
| 3,782,964 | 1/1974 | Knight | 260/112 G X |
| 3,846,397 | 11/1974 | Ernster | 260/112 G X |
| 3,859,451 | 1/1975 | Saunders et al. | 260/112 G X |

OTHER PUBLICATIONS

Arch. Biochemistry, 9, pp. 235–249 (1946), Kneen et al.
Arch. Biochem. 9, pp. 309–320 (1946), Millitzer et al.
Chem. Abstracts, Vol. 75, 1971, 91296p, Schmidt et al.
Chem. Abstracts, Vol. 76, 1972, 83727k, Schmidt et al.

*Primary Examiner*—Howard E. Schain
*Attorney, Agent, or Firm*—M. Howard Silverstein; William Takacs

[57] ABSTRACT

Alpha-amylase inhibitor is prepared from whole wheat or other wheat material by blending the starting material with aqueous alkali, separating the juice therefrom, coagulating and separating a protein concentrate from the juice, and then applying acetone to the residual juice to precipitate the alpha-amylase inhibitor.

2 Claims, No Drawings

PREPARATION OF ALPHA-AMYLASE INHIBITOR

DESCRIPTION OF THE INVENTION

This invention relates to and has among its objects the provision of novel methods for preparing alpha-amylase inhibitor. Further objects of the invention will be evident from the following description wherein parts and percentages are by weight unless otherwise specified.

An alpha-amylase inhibitor, as the name suggests, is a compound which inhibits the action of alpha-amylase, an enzyme which has the ability of hydrolyzing starch into maltose. The inhibitor has many applications. It may be used, for example, in the preparation of rye bread to improve dough development characteristics. In the medical field, the inhibitor has been reported as a serum amylase inhibitor and to have the ability of suppressing hyperglycemia and hyperinsulinemia. Alpha-amylase inhibitor may be used in industrial processes where amylolytic degradation of starch is to be avoided, for example, in the wet milling of corn. A further use of the inhibitor is as a natural larvicide. Wheat-infesting larvae contain alpha-amylase as a digestive aid so that application of the inhibitor to these larvae prevents action of alpha-amylase and thus causes them to die of starvation.

As can be seen from the foregoing, the uses of alpha-amylase are manifold. Presently, however, the cost of the inhibitor is prohibitive because of the high cost of known methods for preparing it. Because of these economic factors, the inhibitor cannot be used in many applications where it would be advantageous to do so.

The invention described herein provides a means for obviating the above problem. By application of the invention, alpha-amylase inhibitor in a highly-active form can be prepared inexpensively and in large quantities from wheat material, which term is used herein in a generic sense to include wheat grains, wheat flour, and wheat millfeeds, that is, the by-products of wheat milling such as bran, shorts, middlings, red dog, and the like. Additionally, by the same process, alpha-amylase inhibitor can be prepared from rye and sorghum material.

The process of the invention includes certain steps in common with those disclosed in the co-pending application of Robert M. Saunders et al. Ser. No. 399,892, filed Sept. 24, 1973, now U.S. Pat. No. 3,859,451, a continuation-in-part of Ser. No. 283,690, filed Aug. 25, 1972, now abandoned. The disclosures of said prior applications are included herein by reference. These common steps are as follows: Wheat material is intimately mixed with aqueous alkali, and the juice is then separated from the resulting mixture. This juice is acidified. Steam is injected into the acidified juice to coagulate a solid protein concentrate which is separated from residual juice. The protein concentrate is the desired product of the prior applications.

Our investigations have shown that the residual juice (that remaining after separation of the solid protein concentrate) contains the alpha-amylase inhibitor. This is a surprising discovery because it would have been expected that the inhibitor (being itself a protein) would be either destroyed by the coagulation or precipitated along with the protein concentrate and thus be associated with this product rather than remaining in the residual juice. We have found, moreover, that the alpha-amylase inhibitor can be readily precipitated from the residual juice by addition of acetone. Thus in accordance with the invention, acetone is mixed with the aforesaid residual juice whereby the alpha-amylase inhibitor contained therein is precipitated and can be readily separated from the remaining liquid.

The primary advantage of the invention is its simplicity. Highly-active alpha-amylase inhibitor can be prepared in one day or less, whereas known methods—which involve fractionation with concentrated ammonium sulphate followed by treatments including dialysis to remove excess salts—are so complex that they require 7 to 14 days. The invention has further economic advantages in that the inhibitor can be prepared from inexpensive starting materials—namely, wheat millfeeds—and it yields as a by-product protein concentrates which are valuable for fortifying foods of all kinds.

Another advantage is that the alpha-amylase inhibitor produced in accordance with the invention displays increased activity over that of the inhibitor prepared by known methods. Thus the inhibitor of the invention is not only more economically produced, but it is also more active than the commercially-available product. Moreover, the inhibitor produced in accordance with the invention is completely soluble in water, whereas the commercial product is at most 50% soluble in water.

DETAILED DESCRIPTION OF THE INVENTION

The practice of the invention is described below in detail.

a. In a first step, wheat material is mixed with aqueous alkali to obtain a pH of 8 to 9. If necessary, the wheat material is ground prior to mixing with the alkali solution. Grinding is used, for example, where the material is wheat in whole or broken grain form. Ammonia, ammonium hydroxide, sodium hydroxide, potassium hydroxide, and the like are suitable alkalis. The alkali is preferably first dissolved in water, and the resulting aqueous solution mixed with the wheat material. Water is applied in the proportion of about 3 to 5 lbs. thereof per pound of wheat material. Contact between the wheat material and the aqueous alkali is maintained for about 10 to 20 minutes. Sodium or potassium bisulfite may be added to the mixture to improve the yield and quality of the protein concentrate obtained as a by-product in the practice of this invention. The amount of bisulphite is generally 0.1 to 1% based on the weight of wheat material.

b. Following treatment with alkali, the mixture is filtered under high pressure using a porous bag known in the art as a filter cloth. Generally, pressures of 25 to 100 psi. are employed. However, it should be pointed out that any conventional means for separating juice from solids can be used. Thus, centrifugation is an alternative to the filtration described above. Other methods will be apparent to those skilled in the art.

c. Next, the pH of the juice from above is adjusted to a level of 5.0 to 6.0 by the application of acid. Any food-grade acid can be used. Thus, one may apply hydrochloric acid, sulfuric acid, phosphoric acid, citric acid, tartaric acid, and the like to achieve the desired pH.

d. Following the pH adjustment, steam is applied to the juice to attain a temperature of 80° C. Application of the steam is accomplished by injection into the juice. The steam acts to coagulate a protein concentrate which, as noted above, constitutes a valuable by-product of this invention.

e. The coagulated protein concentrate is separated from the juice by any such conventional procedures as centrifugation, decantation, filtration, etc.

As noted hereinabove, Steps (a) to (e) are essentially those described in the cited prior applications, and no novelty is claimed in them as such.

f. The residual juice remaining after removal of the protein concentrate is then treated to isolate the desired product. To this end, acetone is mixed with the juice in the proportion of 2 volumes of acetone per volume of juice, whereby to precipitate the alpha-amylase inhibitor.

g. The precipitated inhibitor is collected by any such conventional procedure as filtration or centrifugation or decanting. Following its collection, the product is washed with a solution of 2 volumes acetone and 1 volume of water, and then washed with pure acetone. After this washing, the product is air-dried to remove its content of acetone.

The character of the isolated alpha-amylase inhibitors varies somewhat according to the source, i.e., whether the inhibitor is isolated from whole wheat, wheat millfeed, or wheat flour. Generally, the inhibitor will contain about 35 to 50% protein and will have an activity which varies from $10^4$ to $10^5$ units of activity per gram of protein (activity measurements will be explained hereinafter). The products of the invention also contain carbohydrate material but this is of no moment as it does not interfere with their use.

The invention is further demonstrated by the following illustrative example.

EXAMPLE

Preparation of Alpha-amylase Inhibitor

Whole wheat was ground through a 20-mesh screen and 100 g. of the ground wheat was placed in 500 ml. of water. The pH was adjusted to 9 with 3 N NaOH and the mixture was stirred for 15 minutes. Afterwards, the mixture was placed in a filter cloth bag and a pressure of 100 psi. was applied to the mixture to force the juice through the porous filter cloth. The extruded juice was treated with 1 N HCl to adjust the pH to 6.0. Steam was injected into the juice until the temperature thereof reached 80° C. After cooling to room temperature, the mixture was centrifuged for 10 minutes at 4000 x g to remove the precipitated protein concentrate.

The supernatant liquid which was thus separated from the precipitated protein concentrate, was mixed with 2 volumes of acetone. A white precipitate formed and was collected by filtration. The precipitated inhibitor was washed first with 200 ml. of a 2:1 acetone-water mixture and then with 100 ml. of pure acetone. The product, a fine white powder, was dried. The product was completely soluble in water and was devoid of protease activity.

The above procedure was also applied to wheat shorts, wheat flour, and red dog (a wheat flour-milling by-product containing wheat bran and a small amount of wheat flour). The yields, protein content, and total units of alpha-amylase inhibitory activity are summarized in the table below.

The activity of the inhibitor is defined as follows: 1 unit of activity is the quantity of inhibitor required to cause 66% inhibiton of 3.73 units of chick pancreas alpha-amylase. 1 unit of amylase is the amount of amylase required to liberate 1 mg. of maltose from starch in 10 minutes. Inhibitory activity was assayed as follows: The inhibitor (amount equivalent to 5 micrograms of protein) in 0.02 M sodium barbiturate buffer (pH 7) containing 0.15 M sodium chloride was incubated with chick pancreas alphaamylase for 30 minutes. Then, 10 mg. of soluble starch was added to initiate the enzyme reaction. After a period of digestion of 10 minutes, the extent of starch digestion was measured with dinitrosalicylic acid reagent.

| Source | Yield (%) | Protein* (%) | Units of activity per gram of protein |
|---|---|---|---|
| Wheat flour | 1.00 | 36.3 | $11.00 \times 10^4$ |
| Whole wheat | 0.63 | 48.8 | $6.35 \times 10^4$ |
| Red dog | 1.84 | 38.8 | $4.89 \times 10^4$ |
| Wheat shorts | 2.60 | 33.1 | $1.15 \times 10^4$ |

*N × 6.25

Having thus described the invention, what is claimed is:

1. A process for preparing alpha-amylase inhibitor, which comprises
  a. applying an aqueous alkalizer to wheat material to adjust to a pH 8 to 9,
  b. pressing a juice containing soluble proteins therefrom,
  c. acidifying the juice to a pH of 5.0 to 6.0,
  d. coagulating a solid protein concentrate within the juice by applying steam to the juice until its temperature is raised to 80° C.,
  e. separating the so-coagulated solid protein concentrate from the juice,
  f. adding acetone to the residual juice to precipitate the alpha-amylase inhibitor contained therein, and
  g. separating the precipitated alpha-amylase inhibitor from the juice.

2. A process for preparing from wheat millfeed both alpha-amylase inhibitor and a stable protein concentrate useful as a human food supplement, which comprises
  a. applying an aqueous alkalizer to the wheat millfeed to adjust to a pH of 8 to 9,
  b. pressing a juice containing soluble proteins therefrom,
  c. acidifying the juice to a pH of 5.0 to 6.0,
  d. coagulating a solid protein concentrate within the juice by applying steam to the juice until its temperature is raised to 80° C.,
  e. separating the so-coagulated solid protein concentrate from the juice,
  f. adding acetone to the residual juice, in the proportion of 2 volumes acetone per volume of juice, to precipitate the alpha-amylase inhibitor contained therein, and
  g. separating the precipitated alpha-amylase inhibitor from the juice.

* * * * *